(12) United States Patent
Goetz et al.

(10) Patent No.: US 8,700,157 B2
(45) Date of Patent: Apr. 15, 2014

(54) TELEMETRY HEAD PROGRAMMER FOR IMPLANTABLE MEDICAL DEVICE AND SYSTEM AND METHOD

(75) Inventors: Steven M. Goetz, Brooklyn Center, MN (US); Duane Bourget, Albertville, MN (US)

(73) Assignee: Medtronic, Inc., Minneapolis, MN (US)

( * ) Notice: Subject to any disclaimer, the term of this patent is extended or adjusted under 35 U.S.C. 154(b) by 1527 days.

(21) Appl. No.: 11/119,423

(22) Filed: Apr. 29, 2005

(65) Prior Publication Data

US 2006/0247710 A1   Nov. 2, 2006

(51) Int. Cl.
*A61N 1/00* (2006.01)

(52) U.S. Cl.
USPC .......................................................... 607/32

(58) Field of Classification Search
USPC ................... 607/30, 32, 60, 59; 128/903, 904
See application file for complete search history.

(56) References Cited

U.S. PATENT DOCUMENTS

| | | | | |
|---|---|---|---|---|
| 4,245,641 A * | 1/1981 | Mann et al. | ...................... | 607/30 |
| 4,809,697 A * | 3/1989 | Causey et al. | ..................... | 607/31 |
| 5,507,786 A * | 4/1996 | Morgan et al. | ................... | 607/27 |
| 5,720,770 A | 2/1998 | Nappholz et al. | | |
| 5,722,999 A * | 3/1998 | Snell | ............................... | 607/32 |
| 5,899,931 A * | 5/1999 | Deschamp et al. | .............. | 607/60 |
| 6,263,245 B1 * | 7/2001 | Snell | ............................... | 607/60 |
| 6,327,501 B1 * | 12/2001 | Levine et al. | .................... | 607/27 |
| 6,443,891 B1 * | 9/2002 | Grevious | ........................ | 600/302 |
| 6,641,533 B2 | 11/2003 | Causey et al. | | |
| 6,650,941 B2 * | 11/2003 | Ferek-Petric | .................... | 607/30 |
| 6,780,156 B2 | 8/2004 | Haueter et al. | | |
| 7,103,414 B1 * | 9/2006 | Poore et al. | ...................... | 607/32 |
| 2003/0135246 A1 | 7/2003 | Mass et al. | | |
| 2003/0174066 A1 * | 9/2003 | Goetz et al. | ............... | 340/870.01 |
| 2003/0220673 A1 | 11/2003 | Snell | | |
| 2004/0106967 A1 | 6/2004 | Von Arx et al. | | |
| 2004/0147969 A1 | 7/2004 | Mann et al. | | |

FOREIGN PATENT DOCUMENTS

| | | |
|---|---|---|
| WO | WO 93/09841 | 5/1993 |
| WO | WO 01/52934 | 7/2001 |
| WO | WO 01/52934 A1 | 7/2001 |
| WO | WO 02/68047 | 6/2002 |
| WO | WO 02/100262 A1 | 12/2002 |
| WO | WO 03/095024 | 11/2003 |

OTHER PUBLICATIONS

European Examination Report for EP 06 758 777.4, Jan. 24, 2012.

* cited by examiner

*Primary Examiner* — Christopher D Koharski
*Assistant Examiner* — Roland Dinga
(74) *Attorney, Agent, or Firm* — IPLM Group, P.A.

(57) ABSTRACT

System, telemetry head and method for programming an implantable medical device adapted to provide a therapeutic output to a patient, the implantable medical device being programmable through a telemetry interface. A telemetry head is adapted for transcutaneous communication with the implantable medical device through the telemetry interface when the telemetry head is positioned with respect to the implantable medical device. A computing device has computing processing power and a user interface linked with the telemetry head. The computing device processes the computing instructions associated with the implantable medical device. The computing device supplies the user interface based, at least in part, on the computing instructions associated with the implantable medical device. The telemetry head receives programming instructions from the computing device and provides the programming instructions to the implantable medical device using the transcutaneous telemetry interface.

16 Claims, 5 Drawing Sheets

TELEMETRY HEAD PROGRAMMER FOR IMPLANTABLE MEDICAL DEVICE AND SYSTEM AND METHOD

FIELD OF THE INVENTION

The present invention relates generally to programmers for implantable medical devices and, more particularly, to programmers for implantable medical devices using transcutaneous telemetry.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Some of these devices, if not all, and other devices either provide an electrical output or otherwise contain electrical circuitry to perform their intended function.

Typically, an external device, commonly known as a programmer, is used to interface with an implanted medical device using a communication scheme, usually called telemetry. Such an external programmer can be used for any number of tasks associated with an implanted medical, including, but not limited to, obtaining information about the condition, state or status of the implanted medical device, obtaining information about the patient, including information related to the treatment intended to be provided by the implanted medical device, sending information directed or, at least in part, specifying the treatment parameters and conditions being or to be provided by the implanted medical device, sending or updating maintenance information concerning the implanted medical device. In short, an external programmer is intended to perform any and all communication functions necessary or desired with an implanted medical device which otherwise could be done more directed if the medical device were not implanted.

Such an external programming device may typically consist of several different components performing several different functions. The external programming device may have a telemetry module containing components necessary for conducting the communication protocol with the implanted medical device. Many different telemetry communication protocols exist and the external programming device contains the external circuitry necessary to provide such transcutaneous communication. The external programmer can also contain the necessary interface for the user of the programmer. Typically, the user interface will consist of control inputs and information outputs. Control inputs can consist of buttons, discrete or soft, screen inputs (cursor, mouse, trackball, pointer, etc.), text input, voice input, and other well known input techniques. Information outputs may typically consist of well known outputs such as visual, auditory or tactile, including lights, screens, including liquid crystal display screens or light emitting diode displays, icons, text, synthesized voice, graphs, colors and the like. The external programmer will typically also contain programming instructions for generating and processing the user interface and processing information received from the implanted medical device and generating commands or information to be sent to the implanted medical device. Typically, these programming instructions are contained in program code which is executed in some form of processing module, or CPU.

As can be seen, an external programmer can be quite complex. Further, it is desirable to make the external programmer generally portable for that the programmer can easily be used in the proximity of the patient having the implanted medical device. Ease of portability generally means relatively small size and weight.

Further, different implantable medical devices have differing telemetry protocol communication schemes. And the user interface and the programming logic of the external programmer will also typically vary among differing implantable medical devices.

The competing needs of portability and complex function generally have meant that external programmers have been individually developed for each specific implantable medical device. That is, an external programmer developed for one implantable medical device won't necessarily work advantageously for a different type of implantable medical device.

The cost necessary to develop an individual external programmer for each type of implantable medical device needlessly adds to the cost of medical treatment. The time and resources necessary to develop an individual external programmer may slow the availability of medical treatment to the patient.

U.S. Pat. No. 5,720,770, Nappholz et al, Cardiac Stimulation System With Enhanced Communication and Control Capability, discloses a cardiac stimulation system is provided which delivers long term cardiac therapy without a personal supervision by a physician. The system includes a cardiac stimulation device implanted in a patient and an external device in constant or periodic communication with the cardiac device. The external device is used to control the pacemaker operation. The external device receives updates of the condition of the patient and the operation of the cardiac device and the therapy provided by the cardiac device. This information is transmitted by the external device over a standard telephone network which may consist of hardwired network, a cellular network, or a combination thereof to a remote control device operating near the physician and/or a monitoring station used for monitoring and data logging information from a plurality of patients. The cardiac device, through the external device can also communicate directly and exchange information with the patient over an RF channel. Finally, the external device may be provided with ground position indication system for locating the patient geographically in an emergency.

U.S. Pat. No. 6,263,245, Snell, System and Method for Portable Implantable Device Interrogation, discloses a system and method for obtaining data from an implantable medical device and delivering the data to a data processing device. A portable interrogation device conducts a wireless interrogation of an implantable medical device implanted in a patient and stores the data received from the implantable medical device in a memory of the portable interrogation device. At a later time, the portable interrogation device is directly interfaced with a data processing device using a high-speed connection, which provides the data processing device with high-speed access to the interrogated data that is stored in the portable interrogation device's memory.

U.S. Pat. No. 6,641,533, Causey et al, Handheld Personal Data Assistant With a Medical Device and Method of Using Same, discloses a medical device module for use in a system with a remote programmer and/or a personal data assistant (PDA) with at least one medical device includes a housing, at least one medical device and a processor. The housing is adapted to couple with the PDA. The at least one medical device interface is coupled to the housing for interfacing with the at least one medical device. The processor is coupled to the at least one medical device interface to process data from the at least one medical device. The processor is also capable of interfacing with the PDA.

U.S. Pat. No. 6,780,156, Haueter et al, Module For a Computer Interface, discloses a module for a computer interface including a transducer wherein the transducer receives a measurement and makes this measurement value available for monitoring an individual's health by means of a computer interface, for example, for monitoring an individual's blood glucose level, wherein the measurement value is obtained by means of a sensor.

PCT Patent Application No. WO 01/052934, Medtronic, System and Method For Communicating Between an Implantable Medical Device and a Remote Computer System or Health Care Provider, discloses a medical information communication system. The system permits monitoring the performance of an implantable medical device implanted within the body of a patient, monitoring the health of the patient, or remotely delivering a therapy to the patient through the implantable medical device. The implantable medical device is capable of bidirectional communication with a communication module, a mobile telephone or a personal data assistant located outside of the patient's body.

PCT Patent Application No. WO 03/095024, Medtronic, Seamless Communication Between an Implantable Medical Device and a Remote System, discloses a communications scheme in which a remote computer or computer system, or a remote health care provider, communicates with an implantable medical device implanted within a patient by communicating through a mobile telephone and/or PDA and a communication module located near the patient, where the communication module is operatively connected to the mobile telephone and/or PDA and is capable of telemetrically uploading and downloading information to and from the implantable medical device, and thence via the mobile telephone or PDA to the remote computer or health care provider. In some embodiments, communications between the remote computer system or remote health care provider and the implantable medical device include remotely debugging, updating or installing new software in the implantable medical device or the communication module.

PCT Patent Application No. WO 93/09841, Cyberonics, Activation Techniques for Implantable Medical Device, discloses apparatus and techniques for activating an implantable medical device, such as a neurostimulator adapted to treat and control a disorder by a patient where the disorder is susceptible to relief in response to a predetermined modulation of the electrical activity of a selected nerve or group of nerves of a patient. The neurostimulator includes a stimulus generator, when activated, to generate a programmable electrical waveform, and an electrode array electrically connected to the stimulus generator for delivering the selected waveform to a selected nerve of the patient, such as the vagus nerve. The neurostimulator is also adapted to be programmed to provide the waveform with parameter values selected to stimulate the selected nerve to produce the predetermined modulation of the nerve's electrical activity. The neurostimulator is activated to respond to a patient initiated signal which may be derived either manually or automatically to selectively activate the stimulus parameter.

The use general purpose computing devices to program implanted medical devices is also problematic. If a general purpose computing device is utilized, the medical device manufacturer may lose control over the device programming environment. The specific character of the general computing device is not known and it is not known what other programs may exist on the general computing device or the security of the general computing device.

BRIEF SUMMARY OF THE INVENTION

The present invention provides a telemetry head, system and method that can be used and re-used on multiple types of implantable medical devices to provide external programming functions without the necessity of developing a unique programmer for each type of implantable medical device. Further, the telemetry head, system and method of the present invention take advantage of the use of currently existing, commonly available general computing device without encountering many of the dangers associated with using a general computing device over which the manufacturer of the external programmer and/or the implantable medical device has no control.

Often times, the functions of an external programmer are separated into two physical components. The user interface, programming instructions, the processing power and the circuitry needed for telemetry communications with the implanted medical device are contained in one physical component that is connected, typically by an umbilical cord, to a telemetry head containing, generally, only an antenna for transcutaneous communication.

The present invention utilizes a specific telemetry head containing the specific circuitry needed for transcutaneous communication with an implantable medical device and having computing instructions used for determining programming information for the implantable medical device. The telemetry head communicates with a general computing device that provides user interface and computational resources while obtaining computing instructions from the telemetry head. Because the computing instructions are associated with the telemetry, and are not a program run from the general computing device, control over the programming process can be maintained without the necessity of having computing resources and user interface resources tied up in a dedicated external programmer dedicated to a particular type of implantable medical device. Only the telemetry head needs to be specific to a type of implantable medical device which makes the development of the telemetry less costly and faster.

An embodiment of the present invention provides a system for programming an implantable medical device adapted to provide a therapeutic output to a patient, the implantable medical device being programmable through a telemetry interface. A telemetry head is adapted for transcutaneous communication with the implantable medical device through the telemetry interface when the telemetry head is positioned with respect to the implantable medical device. A computing device has computing processing power and a user interface linked with the telemetry head. The computing device processes the computing instructions associated with the implantable medical device. The computing device supplies the user interface based, at least in part, on the computing instructions associated with the implantable medical device. The telemetry head receives programming instructions from the computing device and provides the programming instructions to the implantable medical device using the transcutaneous telemetry interface.

An alternative embodiment of the present invention provides a telemetry head adapted for programming an implantable medical device programmable through a telemetry interface. A telemetry interface is complementary with the telemetry interface of the implantable medical device and is adapted to provide transcutaneous telemetry with the implantable medical when the telemetry head is positioned with respect to the telemetry interface of the implantable medical device. Computing instructions are associated with the telemetry head related to programming of the implantable medical device. A communication link is capable of communication between the telemetry head and a computing device. The telemetry head makes the computing instructions available to the computing device so that the computing device may provide a user with a user interface relative to programming of the implantable medical device and so that the computing device may compute programming instructions based, in part, upon computing instructions received from the telemetry head and, in part, on input from the user interface. The telemetry head is adapted to receive the programming instructions from the computing device. The telemetry head is adapted to provide the programming instructions to the implantable medical device using the transcutaneous telemetry interface.

An alternative embodiment of the present invention provides a method of programming an implantable medical device adapted to provide a therapeutic output to a patient, the implantable medical device being programmable through a telemetry interface. Computing instructions related to programming of the implantable medical device are transmitted from the telemetry head to a computing device having computing processing power and a user interface. The user interface is generated based, in at least in part, on the computing instructions. Programming instructions for the implantable medical device are created using the computing processing power of the computing device, the programming instructions based, in part, on the computing instructions and, in part, on input from the user interface. The programming instructions are transmitted from the computing device to the telemetry head. The programming instructions are transcutaneously transferred from the telemetry head to the implantable medical device through the telemetry interface.

An alternative embodiment of the present invention provides a set of computing instructions contained in a storage medium associated with a telemetry head adapted for programming an implantable medical device programmable through a telemetry interface. The computing instructions transmit the computing instructions related to programming of the implantable medical device from the telemetry head to a computing device having computing processing power and a user interface; generate the user interface based, in at least in part, on the computing instructions; create programming instructions for the implantable medical device using the computing processing power of the computing device, the programming instructions based, in part, on the computing instructions and, in part, on input from the user interface; transmit the programming instructions from the computing device to the telemetry head; and transcutaneously transfer the programming instructions from the telemetry head to the implantable medical device through the telemetry interface.

In a preferred embodiment, the computing instructions are contained within the telemetry head.

In a preferred embodiment, a data storage element is associated with the telemetry head, the data storage element storing data associated with programming of the implantable medical device.

In a preferred embodiment, the data associated with programming of the implantable medical device comprises data specifying, at least in part, programming steps to be carried out by the implantable medical device.

In a preferred embodiment, the data associated with programming of the implantable medical device comprises patient information.

In a preferred embodiment, patient information is encrypted.

In a preferred embodiment, the data associated with programming of the implantable medical device is stored within the telemetry head.

In a preferred embodiment, the telemetry head acts as a file system supplying the computing instructions to the computing device.

In a preferred embodiment, the telemetry head is adapted for programming of a plurality of types of implantable medical devices and wherein the computing instructions directs the computing device to present a user interface that allows a user to select one of the plurality of types of implantable medical devices which the user elects to program.

DETAILED DESCRIPTION OF THE INVENTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of data transmission protocols and that the systems and protocols described herein represent specific examples for the invention.

For the sake of brevity, conventional techniques related to implantable medical device telemetry, implantable medical device data processing, data communication protocols, computer network architectures, user interface generation and manipulation, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

Figure 1:
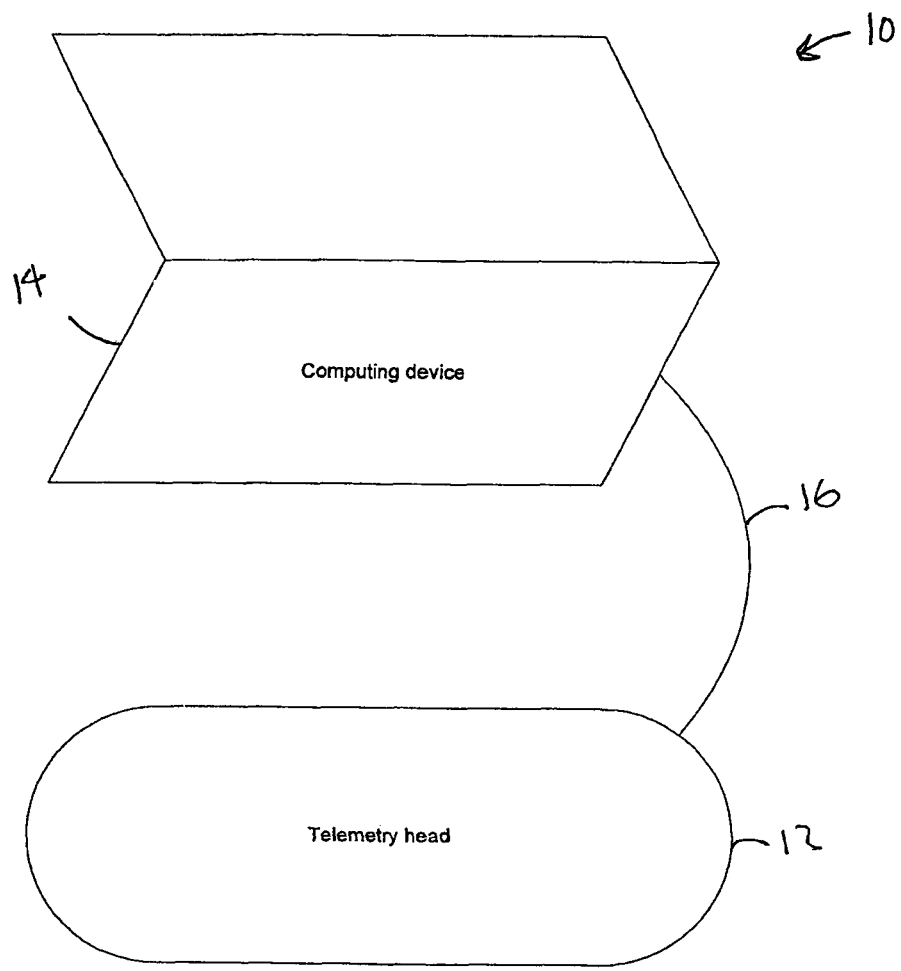
FIG. 1 is a functional block diagram of an embodiment of the present invention.

As shown in the system 10 illustrated in FIG. 1, an embodiment of the present invention leverages telemetry head 12 containing circuitry adapted for transcutaneous communication with an implantable medical device, e.g., telemetry, when telemetry head 12 is positioned with respect to the implantable medical device, e.g., in proximity of the implantable medical device. The telemetry head 12 also has computing instructions associated with the telemetry, e.g., stored with the telemetry head 12, for developing and/or determining the programming instructions, or programming commands, to be transmitted to the implantable medical device. The telemetry head 12, however, is coupled in communication with computing device 14, e.g., desktop or notebook computer, personal data assistant (PDA), tablet computer, cellular telephone, in order to utilize the user interface and, possibly, the processing power available in, on or associated with computing device 14. Computing device 14 provides the user interface and, possibly, the processing power for the external programming process.

However, the computing instructions necessary for determining the commands and/or information to be provided to the implantable medical device are associated with telemetry head 12. This allows telemetry head 12, the component dedicated for programming the implantable medical device, to control the environment in which the external programming of the implantable medical device is performed. This may include specifying the user interface provided to the user performing the programming of the implantable medical device allowing a consistent user interface even though multiple computing devices 14 are utilized to deliver that user interface.

Because the computing instructions for the programming process are associated with telemetry head 12, a computing program need not be loaded onto computing device 14. This allows greater control over the computing environment during programming of the implantable medical device. Telemetry head 12 may essentially take over computing device 14 by running instructions from telemetry head 12 instead of computing device 14 running instructions from a program loaded into memory of computing device 14.

Telemetry head 12 is coupled in communication with computing device 14 through communications link 16. Communications link 16 may be any form of communication able to establish communication between telemetry head 12 and computing device 16. Communications link 16 may be wired or wireless. Examples of wired communications links commonly available include parallel and series interfaces, Ethernet, IEEE 1392 (Firewire) and USB. In a preferred embodiment, communication link 16 is a commonly available USB communication cable. Examples of wireless communications include any of a number of suitable wireless technologies including the 802.11 family of standards, Bluetooth and GPRS.

Computing device 14 generally already contains components facilitating an interface with a user, which in this case is a person or persons associated with programming the implantable medical device. In general, any type of user interface may be utilized including input devices such as buttons, keyboard, mouse, trackball, touch screen, pointer, voice recognition, and similar. Also in general, any type of output may be utilized including visual and audible as well as tactile devices. Examples may include display screens, including CRT and LCD, perhaps including icons, lights, speakers, horns, vibrators and similar.

In a preferred embodiment, computing device 14 also contains processing power, perhaps in the form of a central processing unit or a microprocessor or microchip, for routine administrative tasks, handling the user interface and handling communication with telemetry head 12. It is to be recognized and understood, of course, that various portions or all of parts or all of these functions may also be performed by discrete hardware and/or software components dedicated for their purpose or multiple purposes. Computing device 14 also contains processing power, either on-board or obtaining from a remote source, for executing computing instructions. Typically, these computing instructions are contained in or stored in memory located in computing device or associated with it, such as an external hard drive.

Figure 2:
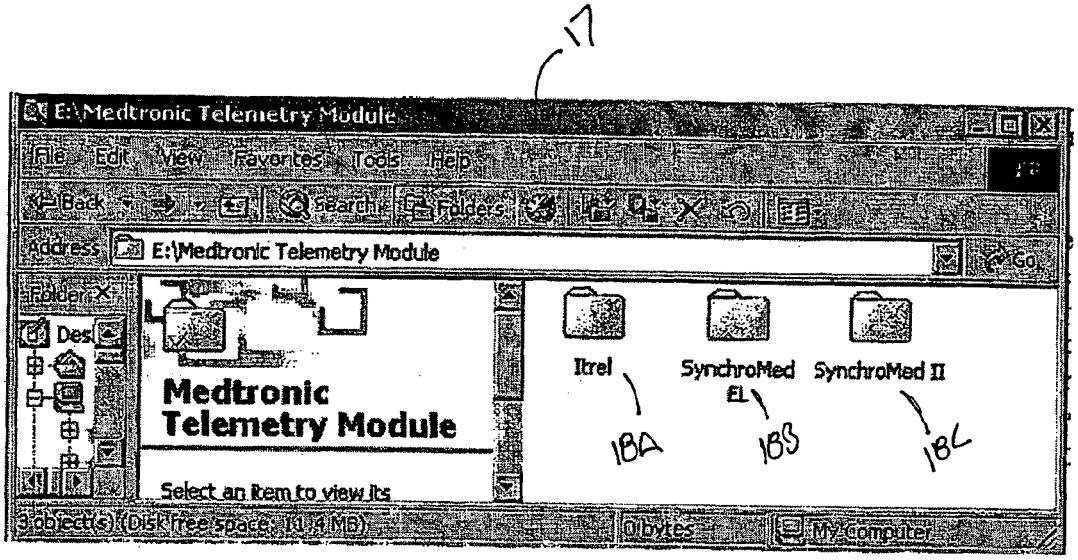
FIG. 2 illustrates a file menu of programming instructions contained in the telemetry head.
Figure 3:
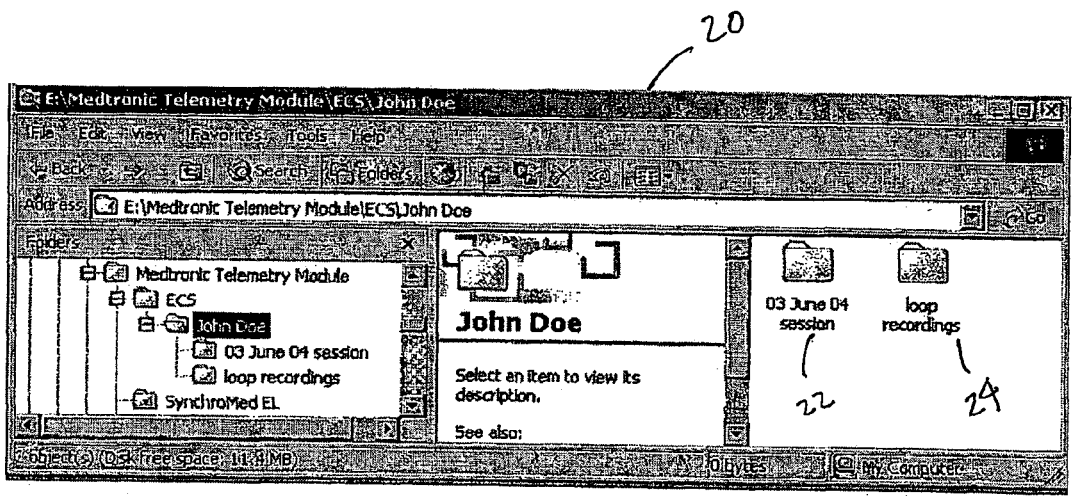
FIG. 3 illustrates a file menu of patient data contained in the telemetry head.

FIG. 2 is an illustration representative of a file folder display 17 showing the contents of a device, in this case telemetry head 12. As shown in FIG. 2, telemetry head 12 contains one or more folders 18, each associated with a particular type or model of implantable medical device. In the illustration represented, telemetry head 12 contains folders associated with a Medtronic Itrel™ implantable medical device (folder 18A), a Medtronic SynchroMed™ EL implantable medical device (folder 18B) and a Medtronic SynchroMed II™ implantable medical device (folder 18C). It is to be recognized and understood, that the particular devices represented are only exemplary and the actual device represented and the number of devices represented may and probably will differ depending on which device or devices are to be programmed.

Each folder 18 contains computing instructions associated with the programmability of the particular implantable medical device or devices to which it pertains. For example, folder 18A contains computing instructions associated with the programmability of the Medtronic Itrel™ implantable medical device.

File folder display 17 could be displayed automatically, or otherwise selected by user, when telemetry head 12 is initially connected to or activated by computing device 14. A user could then select the particular folder 18 associated with the desired implantable medical device to be programmed. For example, if the user desires to program a Medtronic Itrel™ implantable medical device, then the user would select folder 18A. Once selected, computing instructions contained within folder 18A would executed by computing device 14, either directly or by temporarily loading all or a portion of the instructions onto computing device 14. If a preferred embodiment, computing instructions are executed directly from telemetry head 12 without loading a set or an entire set of computing instructions onto computing device 14.

Alternatively, telemetry head could be configured so that computing device 14 would automatically run computing instructions from telemetry head 12. In this case, telemetry head 12 essentially functions as an external drive which could be either "auto-run" or could be configured as a bootable device enabling computing device 14 to "start up" in telemetry head 12.

Once computing instructions from telemetry head 12 have begun to be executed by computing device 14, telemetry head 12 could revert to a more traditional role of being a slave to computing device 14 while acting as the telemetry interface with the implantable medical device.

Computing instructions contained in telemetry head 12 are sufficient to define the user interface presented by computing device 14 and to provide the frame work for determining instructions or data to be sent to the implantable medical device as a result of programming. This data, these commands and/or instructions are commonly referred to herein as programming instructions. This is not to be confused with the computing instructions which are executed or to be executed by computing device 14.

In a preferred embodiment, computing instructions contained in telemetry head 12 are configured such that such instructions are removed from computing device 14, for example at the conclusion of programming of the implantable medical device. So configured, no readily discernable trace of the programming operation would be left upon computing device 14. That is, computing device 14 would be returned, roughly, to its state before being used as a programming tool. This may be important to restrict access to patient critical information on computing device 14 and the potential for future access to such patient information. This also may be important so that computing device 14 may be returned to its other uses in a state similar to which it existed before be used as a programming tool. Patient information may be stored in encrypted form to protect the patient information from access by unauthorized users.

Telemetry head 12 may also contain patient specific data as illustrated in file folder display 20. File folder display 20 contains folders having information, for example, on a particular programming session 22 and for loop recordings 24. Having patient information stored on telemetry head 12 allows computing device 14 to used without containing patient information and helps to prevent access to such patient information from computing device 14 following the programming session.

Figure 4:
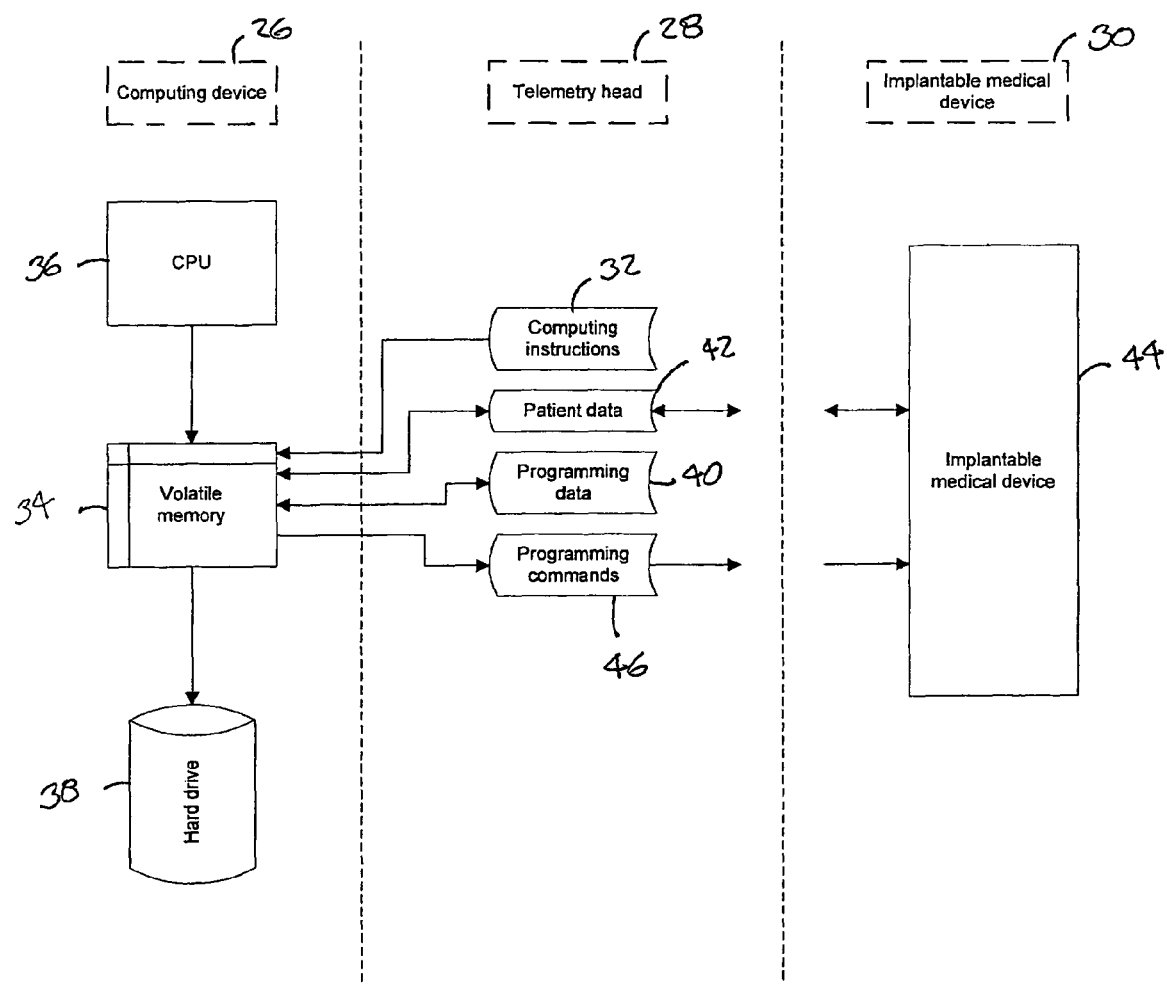
FIG. 4 is a schematic block diagram of the functional components of the computing device, the telemetry head and the implantable medical device.

FIG. 4 illustrates the operation of an embodiment of the present invention in more detail. FIG. 4 is divided into three sections, each representative of three physical components involved in the programming process, namely computing device section 26, telemetry head section 28 and implantable medical device section 30. As shown in telemetry head section 28, telemetry head 12 contains computing instructions 32 which are supplied to computing device 14 in computing device section 26. Computing device 14 holds at least a portion of computing instructions 32 in volatile memory 34. Central processing unit 36 operates on these computing instructions 32 obtained from telemetry head 12. Note that the usual place from which central processing unit 36 would obtain instructions would be associated hard drive 38. It is to be recognized and understood, however, that while the primary intent is for computing device 14 to obtain computing instructions 32 from telemetry head 12 for execution, that computing instructions 32 may also be stored, in whole or in part, in hard drive 38, as well as or instead of volatile memory 34, after being obtained from telemetry head 12. In a preferred embodiment, any computing instructions 32 that are stored, temporarily, in hard drive 38, are deleted, scrubbed or erased from hard drive 38 during or following completion of the programming session. It is also to be recognized and understood, that computing instructions 32 stored in volatile memory 24 may also be temporarily stored in hard drive 38 as part of the virtual memory workings, or other workings, of computing device 14.

Programming data 40, i.e., any other data or information necessary or desired for the programming process which are not actually executable code may also be obtained from and sent back to telemetry head 12. This would include, for example, temporary information used by computing device 14 during the programming process.

As noted above, patient data 42 may be stored on telemetry head 12 for use during programming of implantable medical device 44. Such patient data 42 may reside on telemetry head 12 prior to the programming session as, for example, with a telemetry head 12 wholly or partially dedicated to a particular patient or may be obtained from implantable medical device 44.

Once computing device 14 has determined the proper information and/or instructions to be sent to implantable medical device 44, those programming commands 46 are sent to telemetry head 12 and subsequently forwarded, intact or in modified form, to implantable medical device through the telemetry interface of telemetry head 12.

It should be recognized and understood that computing instructions 32 although shown as being stored in telemetry head 12, may also be stored elsewhere if associated with telemetry head 12. For example, computing instructions 32 could be stored on an external storage device such as an external hard drive, removable disk or memory key. It is also possible that computing instructions 32 could be obtained by telemetry head 12 from an external source such as a wireless communications medium.

Figure 5:
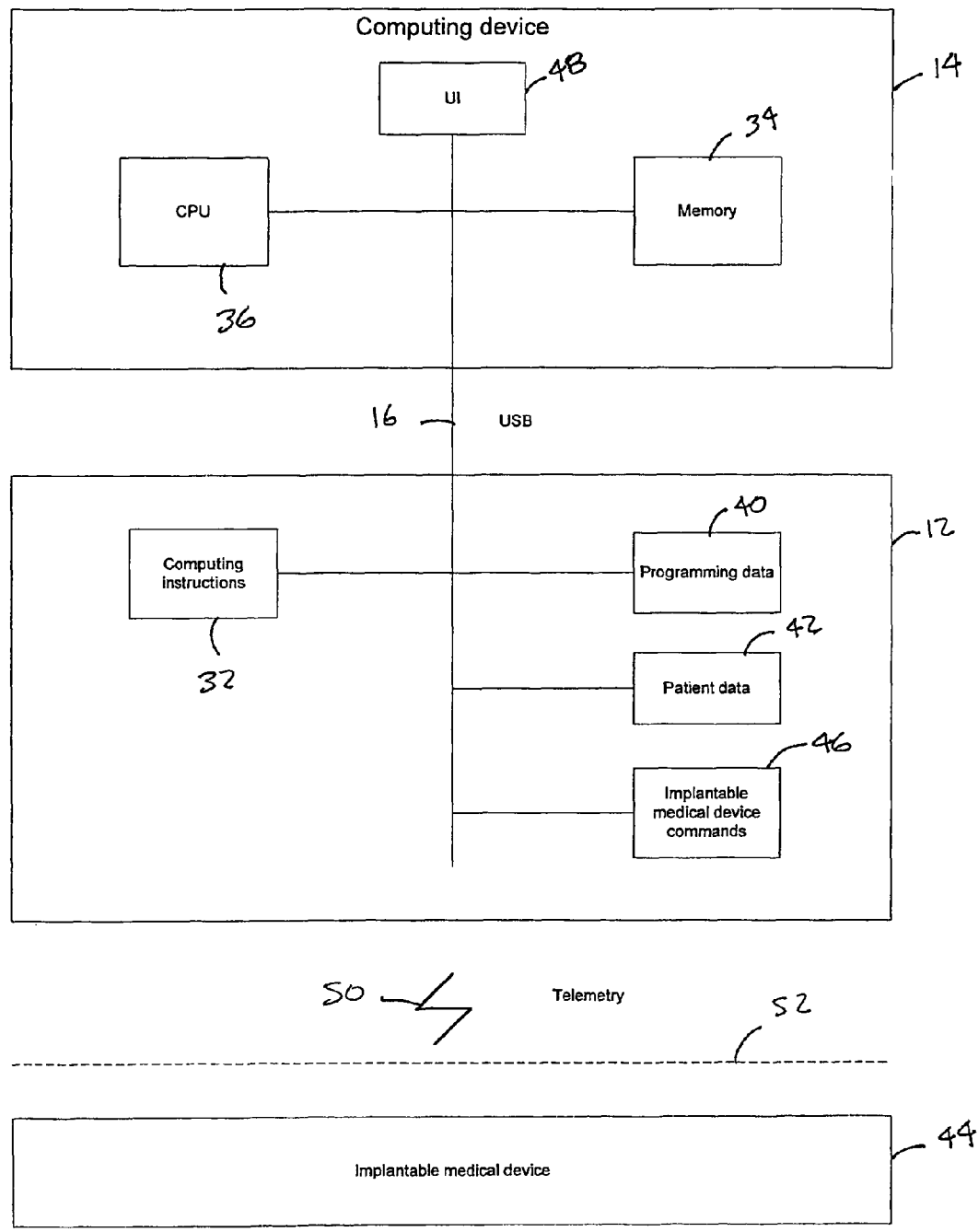
FIG. 5 is a schematic block diagram of an exemplary functional arrangement of components of the computing device and the telemetry head.

FIG. 5 is a schematic representation of programming instructions and data flow. Computing instructions are contained in or associated with telemetry head 12 and are communicated via communications link 16 to computing device 14 and used, alone or in conjunction with programming data 40 and/or patient data 42, in the programming process. Computing device 14 uses its central processing unit 36 and memory 34 to generate user interface 48. Implantable medical device programming commands 46 are generated, perhaps in conjunction with input from user interface 48. Such programming commands 48 are then transmitted by telemetry signal 50 across cutaneous boundary 52 to implantable medical device 44.

Figure 6:
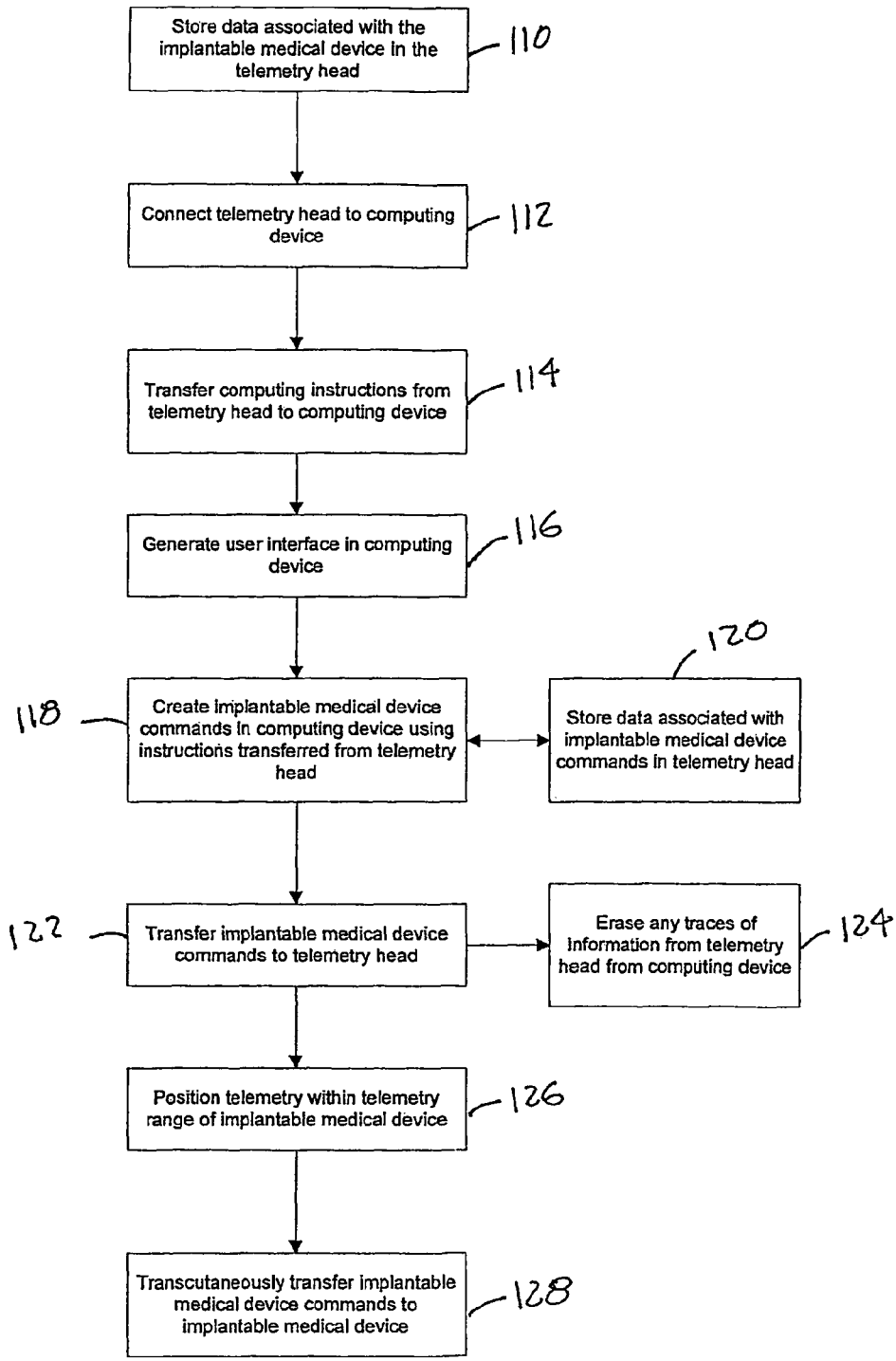
FIG. 6 is a flow diagram of an embodiment of the present invention.

FIG. 6 is a flow chart illustrated the flow of events involved in the programming process. Data is stored (110) associated with telemetry head 12. Telemetry head 12 is connected (112) to computing device 14. Computing instructions 32 are transferred (114) to computing device 14. Computing device 14 generates (116) user interface 48 based, at least in part, on computing instructions 32 obtained from telemetry head 12. Programming commands 46 are generated (118) by computing device 14 using, at least in part, computing instructions 32 obtained from telemetry head 12. Optionally, data associated with implantable medical device 44 may be stored (120) in telemetry head 12. Programming commands 46 for implantable medical device 44 are transferred (122) to telemetry head 12. Preferably, traces of information regarding the programming session are erased (124) from computing device 14. Telemetry head 12 is positioned (126) with respect to implantable medical device 14. Programming commands 46 are transferred (128) by telemetry from telemetry head 12 to implantable medical device 44.

Thus, embodiments of the telemetry head programmer for implantable medical device and system and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for programming an implantable medical device adapted to provide a therapeutic output to a patient, said implantable medical device being programmable through a telemetry interface, comprising:

a telemetry head adapted for transcutaneous communication with said implantable medical device through said telemetry interface when said telemetry head is positioned with respect to said implantable medical device;

a computing device having computing processing power and a user interface;

said telemetry head containing computing instructions related to programming of said implantable medical device;

a communication link between said telemetry head and said computing device;

wherein said computing instructions are transmitted from said telemetry head to said computing device;

wherein said computing device processes said computing instructions received from said telemetry head;

wherein said computing device supplies said user interface based, at least in part, on said computing instructions received from said telemetry head and processed by said implantable medical device; and wherein said telemetry head receives programming instructions from said computing device and provides said programming instructions to said implantable medical device using said transcutaneous telemetry interface.

2. The system of claim 1 further comprising a data storage element associated with said telemetry head, said data storage element storing data associated with programming of said implantable medical device.

3. The system of claim 2 wherein said data associated with programming of said implantable medical device comprises data specifying, at least in part, programming steps to be carried out by said implantable medical device.

4. The system of claim 3 wherein said data associated with programming of said implantable medical device comprises patient information.

5. The system of claim 4 wherein said patient information is stored in encrypted form.

6. The system of claim 3 wherein said data associated with programming of said implantable medical device is stored within said telemetry head.

7. The system of claim 1 wherein said telemetry head acts as a file system supplying said computing instructions to said computing device.

8. The system of claim 1 wherein said telemetry head is adapted for programming of a plurality of types of implantable medical devices and wherein said computing instructions directs said computing device to present a user interface that allows a user to select one of said plurality of types of implantable medical devices which the user elects to program.

9. A telemetry head adapted for programming an implantable medical device programmable through a telemetry interface, comprising:

a telemetry interface complementary with said telemetry interface of said implantable medical device and adapted to provide transcutaneous telemetry with said implantable medical when said telemetry head is positioned with respect to said telemetry interface of said implantable medical device;

computing instructions contained in said telemetry head related to programming of said implantable medical device;

a communication link capable of communication between said telemetry head and a computing device;

wherein said telemetry head supplies said computing instructions from said telemetry head to said computing device and wherein said computing device supplies a user with a user interface relative to programming of said implantable medical device based, in part, upon computing instructions received from said telemetry head and processed by said computing device and, in part, on input from said user interface; and wherein said telemetry head is configured to provide said programming instructions to said implantable medical device using said transcutaneous telemetry interface.

10. The telemetry head of claim 9 further comprising a data storage element associated with said telemetry head, said data storage element storing data associated with programming of said implantable medical device.

11. The telemetry head of claim 10 wherein said data associated with programming of said implantable medical device comprises data specifying, at least in part, programming steps to be carried out by said implantable medical device.

12. The telemetry head of claim 11 wherein said data associated with programming of said implantable medical device comprises patient information.

13. The telemetry head of claim 11 wherein said data associated with programming of said implantable medical device is stored within said telemetry head.

14. The system of claim 12 wherein said patient information is stored in encrypted form.

15. The telemetry head of claim 9 wherein said telemetry head acts as a file system supplying said computing instructions to said computing device.

16. The telemetry head of claim 9 wherein said telemetry head is adapted for programming of a plurality of types of implantable medical devices and wherein said computing instructions directs said computing device to present a user interface that allows a user to select one of said plurality of types of implantable medical devices which the user elects to program.

* * * * *

UNITED STATES PATENT AND TRADEMARK OFFICE
CERTIFICATE OF CORRECTION

| | | |
|---|---|---|
| PATENT NO. | : 8,700,157 B2 | Page 1 of 1 |
| APPLICATION NO. | : 11/119423 | |
| DATED | : April 15, 2014 | |
| INVENTOR(S) | : Goetz et al. | |

It is certified that error appears in the above-identified patent and that said Letters Patent is hereby corrected as shown below:

In the Claims

Col. 12, line 4, Claim 9: "implantable medical when said" should read --implantable medical device when said--

Signed and Sealed this
Fourteenth Day of October, 2014

Michelle K. Lee
*Deputy Director of the United States Patent and Trademark Office*